(12) United States Patent
    Venturini et al.

(10) Patent No.: US 10,624,911 B2
(45) Date of Patent: Apr. 21, 2020

(54) PHYSIOLOGICALLY BALANCED INJECTABLE FORMULATIONS OF FOSNETUPITANT

(71) Applicant: HELSINN HEALTHCARE SA, Lugano/Pazzallo (CH)

(72) Inventors: Alessio Venturini, Varese (IT); Roberta Cannella, Varese (IT)

(73) Assignee: Helsinn Healthcare SA, Lugano/Pazzallo (CH)

( * ) Notice: Subject to any disclaimer, the term of this patent is extended or adjusted under 35 U.S.C. 154(b) by 0 days.

(21) Appl. No.: 15/611,785

(22) Filed: Jun. 2, 2017

(65) Prior Publication Data

US 2017/0348335 A1    Dec. 7, 2017

Related U.S. Application Data

(60) Provisional application No. 62/345,942, filed on Jun. 6, 2016.

(51) Int. Cl.
  *A61K 31/473*  (2006.01)
  *A61K 31/496*  (2006.01)
  *A61K 31/675*  (2006.01)
  *A61K 9/00*  (2006.01)
  *A61K 9/08*  (2006.01)
  *A61K 9/19*  (2006.01)
  *A61K 47/02*  (2006.01)
  *A61K 47/26*  (2006.01)
  *A61K 47/18*  (2017.01)
  *A61P 1/08*  (2006.01)

(52) U.S. Cl.
  CPC .......... *A61K 31/675* (2013.01); *A61K 9/0019* (2013.01); *A61K 9/08* (2013.01); *A61K 9/19* (2013.01); *A61K 31/473* (2013.01); *A61K 31/496* (2013.01); *A61K 47/02* (2013.01); *A61K 47/183* (2013.01); *A61K 47/26* (2013.01); *A61P 1/08* (2018.01)

(58) Field of Classification Search
  CPC .. A61K 31/473; A61K 31/496; A61K 31/675; A61K 9/0019; A61K 9/08; A61K 9/19; A61K 47/02; A61K 47/183; A61K 47/26; A61P 1/08
  See application file for complete search history.

(56) References Cited

U.S. PATENT DOCUMENTS

2010/0048607 A1*  2/2010  Kocherlakota ...... A61K 9/0019
                                                        514/296

FOREIGN PATENT DOCUMENTS

| WO | 95/16679 | 6/1995 |
| WO | 95/18124 | 7/1995 |
| WO | 95/23798 | 9/1995 |
| WO | 2013/082102 | 6/2013 |

OTHER PUBLICATIONS

The New England Journal of Medicine, vol. 340, No. 3 190-195 (1999).
"Tachykinin Receptor and Tachykinin Receptor Antagonists", J. Auton. Pharmacol., 13,23-93, 1993.
Can. J. Phys., 1997, 75, 612-621.
Science, 1998,281, 1640-1645.

* cited by examiner

*Primary Examiner* — Sarah Pihonak
(74) *Attorney, Agent, or Firm* — Clark G. Sullivan

(57) ABSTRACT

Injectable dosages and formulations of fosnetupitant and pharmaceutically acceptable salts thereof are provided that are efficacious, chemically stable and physiologically balanced for safety and efficacy.

21 Claims, 2 Drawing Sheets

PHYSIOLOGICALLY BALANCED INJECTABLE FORMULATIONS OF FOSNETUPITANT

FIELD OF INVENTION

The present invention relates to lyophilized and liquid injectable dosages and formulations of fosnetupitant and pharmaceutically acceptable salts thereof that are efficacious, chemically stable and physiologically balanced for safety and efficacy.

BACKGROUND OF INVENTION

Fosnetupitant is a neurokynin-1 ("NK-1") antagonist under development by Helsinn Healthcare SA, Lugano/Pazzallo Switzerland, for the treatment of chemotherapy induced nausea and vomiting. The active moiety of fosnetupitant, netupitant, is approved in the United States as Akynzeo®, an orally administered capsule that contains 300 mg of netupitant and 0.5 mg palonosetron as palonosetron HCl.

Fosnetupitant is known chemically as 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium. The compound has the following chemical structure in its acidic/free base form:

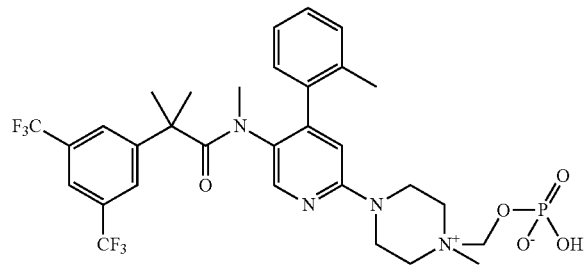 [SMILES: Cc1ccccc1-c1cc(N2CC[N+](C)(COP(=O)([O-])O)CC2)ncc1N(C)C(=O)C(C)(C)c1cc(C(F)(F)F)cc(C(F)(F)F)c1]

The molecular weight of the compound in its free base form is 688.6 g/mol. The molecular weight of the chloride hydrochloride salt is 761.53 g/mol.

A method of preparing fosnetupitant is described in WO 2013/082102. According to WO 2013/082102, the compound was developed partly to overcome injection site issues that occurred when its active moiety (netupitant) was administered as the free base. According to WO 2013/082102, "a single intravenous dose of fosnetupitant is intravenously administered at a dosage of from about 10 mg to about 200 mg, from about 50 mg to about 150 mg, from about 75 mg to about 125 mg, or about 100 mg, based on the weight of the netupitant component of the molecule." In preferred intravenous formulations, the fosnetupitant is reportedly present at a concentration of about 10 mg/mL, again based on the weight of the active moiety.

New intravenous doses and formulations of fosnetupitant are needed for use in the clinic and commercial distribution. However, formulation development is complicated by the degradation of fosnetupitant and some solubility issues. As reported in Table 1 of WO 2013/082102, degradation of the compound can be significant.

The development of fosnetupitant is also complicated by bioavailability issues associated with the parent molecule (netupitant). As reported in the FDA-approved prescribing information for Akynzeo®, "there was a greater than dose-proportional increase in the systemic exposure with the dose increase from 10 mg to 300 mg and a dose-proportional increase in systemic exposure with a dose increase from 300 mg to 450 mg."

A further problem arises in that fosnetupitant (although being more soluble than netupitant), remains a moderately soluble molecule which takes special additives such as surfactants (e.g. polyoxyethylenesorbitan monooleate, etc.) to maintain the product in solution during manufacturing, storage and/or reconstitution in water from solid forms; yet the use of these agents is preferably to be avoided as potentially harmful, in compliance with regulatory safety recommendations. In addition, the present inventors have unexpectedly found, during development studies leading to the present invention, that the solubility of fosnetupitant solutions varies irregularly and unpredictably as a function of small environmental changes (e.g. concentration, temperature, pH, presence of additives like buffers, chelating agents, etc.); the inventors also found that the solubility behavior of fosnetupitant is complicated by its spontaneous partial conversion into the lesser soluble active moiety (netupitant) and/or lesser soluble degradation products: the solubility of such products may respond to criteria different from those optimizing the solubility of fosnetupitant. The overall solubility of fosnetupitant is thus the result of an interplay of different solubilities of different components of the formulation.

Accordingly, it is an object of the invention to provide injection doses of fosnetupitant for the treatment of diseases mediated by the NK1 receptor, including nausea, emesis, and chemotherapy induced nausea and vomiting.

Another object of the present invention is to provide injectable formulations of fosnetupitant with improved stability, solubility, less degradation, and improved physiological tolerance.

Still another object is to provide methods of making injectable formulations of fosnetupitant, and methods of using such formulations in the treatment of diseases modulated by the NK-1 receptor.

Still further objects are to provide formulations that remain stable and soluble when reconstituted with traditional injection media such as glucose and saline.

Still further objects are to provide formulations that remain stable and soluble when formulated and/or stored as solutions; or when formulated and/or stored in solid form; or when reconstituted from solid form with traditional injection media such as glucose and saline.

Additional objects are to provide methods of manufacturing fosnetupitant formulations that protect the final formulation against degradation.

SUMMARY OF THE INVENTION

The inventors have made several important discoveries which enable for the first time lyophilized and liquid injectable formulations of fosnetupitant that are shelf stable and do not cause unwanted injection site reactions. By carefully balancing netupitant and fosnetupitant concentrations in the formulation, and selecting an appropriate pH or appropriate pH adjusting agents for the final solution, an elegant formulation is obtained that remains stable for prolonged periods of time, and does not cause injection site reactions.

Therefore, in a first principal embodiment the invention provides a pharmaceutically stable injectable formulation of fosnetupitant and netupitant at a balanced ratio, as a liquid solution or lyophilized powder, comprising: (a) from 95 to 99.99 weight parts fosnetupitant or a pharmaceutically acceptable salt thereof; and (b) from 0.01 to 5 weight parts netupitant or a pharmaceutically acceptable salt thereof; and (c) pH adjusting means for maintaining said balanced ratio. When the formulation is in an aqueous liquid solution, at a fosnetupitant concentration of approximately 11.8 mg/ml (based on the weight of fosnetupitant free base), said fosnetupitant or pharmaceutically acceptable salt thereof is preferably completely dissolved in said formulation. The pH adjusting means can be characterized by the resulting pH (preferably 7 to 10 in the final formulation), or the agents used to adjust the pH (preferably hydrochloric acid as the acidifying agent and sodium hydroxide as the alkalizing agent).

In another principal embodiment, the invention provides an injectable liquid solution comprising: (a) from 2.3 to 30 mg/mL of fosnetupitant or a pharmaceutically acceptable salt thereof, based on the weight of the free base (b) optionally, from 5 to 30 µg/mL of palonosetron or a pharmaceutically acceptable salt thereof, based on the weight of the free base; (c) sodium hydroxide; (d) disodium edetate; (e) optionally hydrochloric acid; (f) mannitol; and (g) water q.s.

In another principal embodiment, the invention provides an injectable lyophilized powder which, when reconstituted to a suitable volume, comprises (a) from 2.3 to 30 mg/mL of fosnetupitant or a pharmaceutically acceptable salt thereof, based on the weight of the free base; (b) optionally, from 5 to 50 µg/mL of palonosetron or a pharmaceutically acceptable salt thereof, based on the weight of the free base; (c) sodium hydroxide; (d) disodium edetate; (e) optionally hydrochloric acid; and (f) mannitol.

Other embodiments provide a single unit dose injectable formulation of fosnetupitant (liquid or lyophilized powder) comprising approximately 235 mg of fosnetupitant or a pharmaceutically acceptable salt thereof, based on the weight of the free base (corresponding to a 260 mg weight of the salt, in case of the chloride hydrochloride salt of fosnetupitant). Still further embodiments provide a method of treating emesis in a human subject in need thereof by administering an intravenous dose of approximately 235 mg of fosnetupitant, or a pharmaceutically acceptable salt thereof, based on the weight of the free base of fosnetupitant.

Still other embodiments provide methods of manufacturing the formulation to provide a stable, safe and effective formulation. Thus, in one embodiment the invention provides a method of manufacturing a liquid injectable formulation of fosnetupitant comprising: (a) admixing the chloride hydrochloride salt of fosnetupitant with sodium hydroxide in water at a basic pH to form a solution; (b) reducing the pH of the solution by the addition of one or more acidic pH adjusting agents; and (c) optionally admixing the solution with one or more pharmaceutically acceptable excipients. In a particularly preferred embodiment the one or more acidic pH adjusting agents comprises disodium edetate and/or hydrochloric acid.

Additional advantages of the invention are set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments of the invention and together with the description serve to explain the principles of the invention.

DETAILED DESCRIPTION

Definitions and Use of Terms

Figure 1:
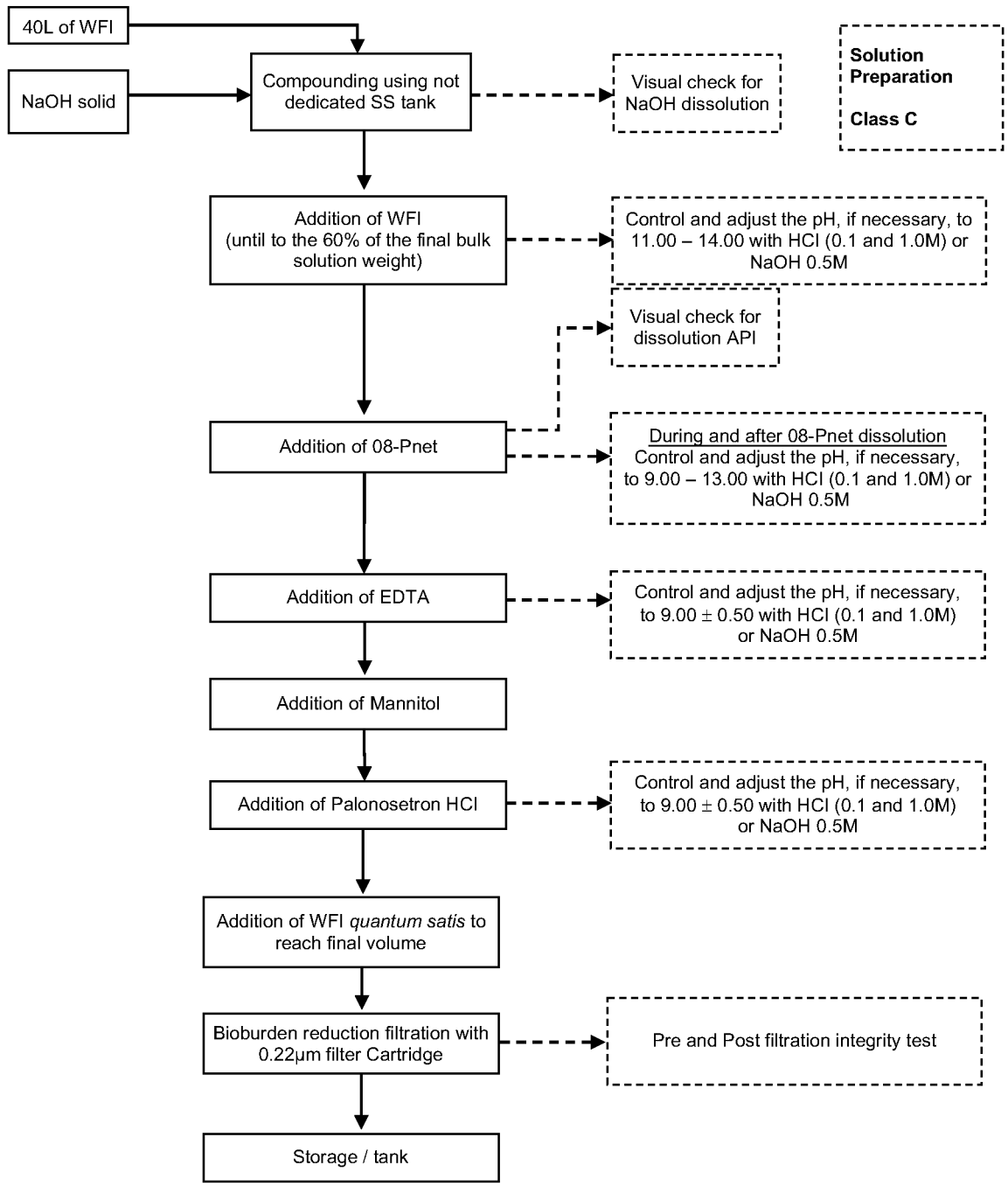
FIGS. 1 and 2 depict a representative process for manufacturing the formulations of the present invention, as described in greater detail in Example 4.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

As used in the specification and claims, the singular forms a, an, and the include plural references unless the context clearly dictates otherwise. For example, the term "a pharmaceutical excipient" refers to one or more pharmaceutical excipients for use in the presently disclosed formulations and methods.

When ranges are given by specifying the lower end of a range separately from the upper end of the range, it will be understood that the range can be defined by selectively combining any one of the lower end variables with any one of the upper end variables that is mathematically possible.

When used herein the term "about" will compensate for variability allowed for in the pharmaceutical industry and inherent in pharmaceutical products, such as differences in product strength due to manufacturing variation and time-induced product degradation. In one embodiment the term allows for any variation which in the practice of pharmaceuticals would allow the product being evaluated to be considered pharmaceutically equivalent or bioequivalent to the recited strength. In another embodiment the term allows for any variation within 5% of the recited strength or concentration of the formulation.

The terms "treating" and "treatment," when used herein, refer to the medical management of a patient with the intent to cure, ameliorate, stabilize, or prevent a disease, pathological condition, or disorder (collectively "disorder"). This term includes active treatment, that is, treatment directed specifically toward the improvement of a disorder, and also includes causal treatment, that is, treatment directed toward removal of the cause of the associated disorder. In addition, this term includes palliative treatment, that is, treatment designed for the relief of symptoms rather than the curing of the disorder; preventative treatment, that is, treatment directed to minimizing or partially or completely inhibiting the development of the disorder; and supportive treatment, that is, treatment employed to supplement another specific therapy directed toward the improvement of the disorder.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. "Pharmaceutically acceptable salts" means salts that are pharmaceutically acceptable, as defined above, and which possess the desired pharmacological activity.

When a weight of an active ingredient is given without reference to the free base or salt of the active ingredient, it will be understood that the weight can refer to the weight of the free base or the weight or the entire salt. In like manner, when the molecule can exist as a hydrate, and the weight of the molecule is given, it will be understood that the weight can be refer to the weight of the hydrate or the weight of the molecule without the waters of hydration.

"Disodium edetate" refers to anhydrous disodium edetate or any of its hydrated forms.

The term "liquid formulation" or "liquid solution" or "injectable solution," or words of similar import, when used in reference to a fosnetupitant injectable solution, refers to any liquid formulation of fosnetupitant that is suitable for intravenous injection. The solution can be manufactured as a liquid and packaged as such, or it can be a formulation that is intended for lyophilization, or a lyophilized formulation reconstituted in water.

Unless differently specified, the term "concentration" means herein the amount of a product present in a volume of solution; when concentration values are given for a lyophilized powder, the concentration values are intended to be based on reconstitution of the powder with a suitable reconstitution volume of water, i.e. the lyophilized powder contains the given product in amounts providing the given concentration values once the powder is dissolved in the reconstitution volume; suitable reconstitution volumes may typically range from 1 to 30 mL, preferably from 3 to 25 mL, more preferably from 8 to 22 mL, such as 19-21 mL or 9-11 mL, for example 10±1 mL or 20±1 mL; other typical reconstitution volumes are 10-30 mL, or 15-25 ml, or about 20 mL.

"Netupitant" refers to 2-(3,5-bis(trifluoromethyl)phenyl)-N,2-dimethyl-N-(6-(4-methylpiperazin-1-yl)-4-(o-tolyl) pyridine-3-yl)propanamide. The compound has a molecular weight of 579 g/mol, and the following chemical structure:

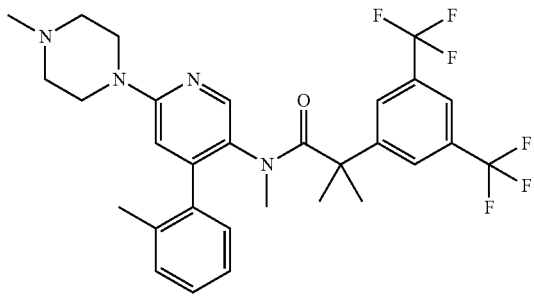 [SMILES: Cc1ccccc1-c1cc(N2CCN(C)CC2)ncc1N(C)C(=O)C(C)(C)c1cc(C(F)(F)F)cc(C(F)(F)F)c1]

Fosnetupitant refers to 4-(5-(2-(3,5-bis(trifluoromethyl) phenyl)-N,2-dimethylpropanamido)-4-(o-tolyl)pyridin-2-yl)-1-methyl-1-((phosphonooxy)methyl) piperazin-1-ium, also referred herein as p-Netu, 08-PNET or API. The compound has the following chemical structure:

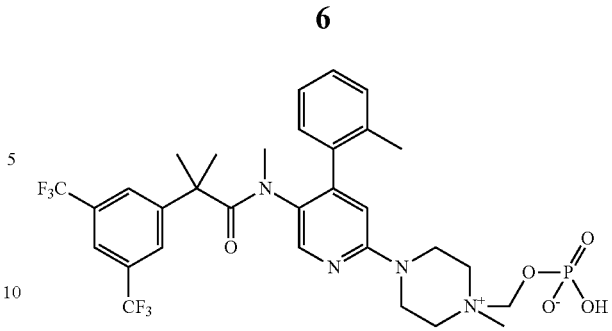

"Palonosetron" refers to (3aS)-2-[(S)-1-azabicyclo [2.2.2] oct-3-yl]-2,3,3a,4,5,6-hexahydro-1-oxolHbenz[de]isoquinoline. The hydrochloride salt has the following chemical structure:

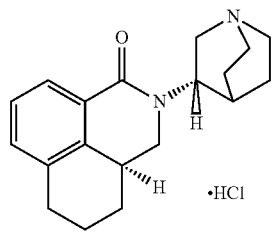 [SMILES: O=C1c2cccc3c2[C@H](CCC3)CN1[C@@H]1CN2CCC1CC2 ; Cl]

Discussion of Principal Embodiments

The invention can be defined based on several principal embodiments which can be combined in any manner physically and mathematically possible to create additional principal embodiments.

In a first principal embodiment the invention provides a pharmaceutically stable injectable formulation of fosnetupitant and netupitant at a balanced ratio comprising: (a) from 95 to 99.99 weight parts fosnetupitant or a pharmaceutically acceptable salt thereof; and (b) from 0.01 to 5 weight parts netupitant or a pharmaceutically acceptable salt thereof; and (c) pH adjusting means for maintaining said physiologically balanced ratio; wherein, when the formulation is a liquid formulation, said fosnetupitant or pharmaceutically acceptable salt thereof is completely dissolved in said formulation.

In another principal embodiment, the invention provides a liquid injectable formulation of fosnetupitant comprising: (a) from 2.3 to 30 mg/mL of fosnetupitant or a pharmaceutically acceptable salt thereof, based on the weight of the free base; (b) optionally, from 5 to 30 µg/mL of palonosetron or a pharmaceutically acceptable salt thereof, based on the weight of the free base; (c) sodium hydroxide; (d) disodium edetate; (e) optionally hydrochloric acid; (f) mannitol; and (g) water q.s.

Another principal embodiment provides a liquid injectable formulation of fosnetupitant comprising: (a) from 2.3 to 30 mg/mL of the chloride hydrochloride salt of fosnetupitant, based on the weight of the free base; (b) optionally from 5 to 50 µg/mL palonosetron hydrochloride based on the weight of the free base; (c) from 0.05 to 0.9 mg/mL disodium edetate (based on the anhydrous form; (d) from 10 to 100 mg/mL mannitol; (e) NaOH and optionally HCl q.s. to pH 7.0-10.0; and (f) water q.s.

Another principal embodiment provides a lyophilized powder injectable formulation of fosnetupitant comprising, when reconstituted in water to a suitable volume: (a) from 2.3 to 30 mg/mL of fosnetupitant or a pharmaceutically acceptable salt thereof, based on the weight of the free base;

(b) optionally, from 5 to 30 µg/mL of palonosetron or a pharmaceutically acceptable salt thereof, based on the weight of the free base; (c) sodium hydroxide; (d) disodium edetate; (e) optionally hydrochloric acid; (f) mannitol;

Still another principal embodiment provides a lyophilized powder injectable formulation of fosnetupitant comprising, when reconstituted in water to a suitable volume: (a) from 2.3 to 30 mg/mL of the chloride hydrochloride salt of fosnetupitant, based on the weight of the free base; (b) optionally from 5 to 50 µg/mL palonosetron hydrochloride based on the weight of the free base; (c) from 0.1 to 2.0 mg/mL disodium edetate (based on the anhydrous form); (d) from 10 to 100 mg/mL mannitol; and (e) NaOH and optionally HCl q.s. to pH 7.0-10.0.

In another principal embodiment, the invention provides a sealed preservative-free vial for a single administration of fosnetupitant comprising: (a) from 100 to 600 mg of fosnetupitant or a pharmaceutically acceptable salt thereof, based on the weight of the free base; and (b) optionally, from 100 to 300 µg of palonosetron or a pharmaceutically acceptable salt thereof, based on the weight of the free base. The formulation within the vial can be a liquid solution or lyophilized powder. A particularly preferred amount of fosnetupitant or a pharmaceutically acceptable salt thereof is 235 mg based on the weight of the free base. Conversely, the invention provides a method of treating emesis by administering an intravenous dose of approximately 235 mg of fosnetupitant, or a pharmaceutically acceptable salt thereof, based on the weight of the free base of fosnetupitant.

In another principal embodiment the invention provides a method of manufacturing an injectable formulation of fosnetupitant comprising: (a) admixing the chloride hydrochloride salt of fosnetupitant with sodium hydroxide in water at a basic pH to form a solution; (b) reducing the pH of the solution by the addition of one or more acidic pH adjusting agents, preferably to a pH still above 7; and (c) optionally admixing the solution with one or more pharmaceutically acceptable excipients, optionally followed by lyophilization.
Discussion of Formulation Subembodiments The invention can further be understood with reference to various subembodiments which can modify any of the principal embodiments. These subembodiments can be combined in any manner that is both mathematically and physically possible to create additional subembodiments, which in turn can modify any of the principal embodiments. For example, any aspect of the formulation given below can be used to further define a liquid solution of the principal embodiments, or a lyophilized powder of the principal embodiments. To the extent the preferred liquid and lyophilized formulations differ, those differences will be called out specifically in the subembodiments.

In any of the foregoing embodiments, the fosnetupitant is preferably present as the chloride hydrochloride salt. However, it will be understood that the fosnetupitant can also be present in the formulation as the free base or any other pharmaceutically acceptable salt. It will also be understood that the salt can disassociate in a liquid medium into ion/counter-ion pairs, and still constitute a "salt" as that term is used in the present document according to industry custom.

Various subembodiments can also be defined based on the concentration of fosnetupitant in the solution. In one subembodiment, the concentration of fosnetupitant or pharmaceutically acceptable salt thereof in solution is from 4.5 to 27 mg/mL based on the weight of the free base. In other subembodiments, the concentration of fosnetupitant in the solution ranges from 6 to 26 mg/mL, 8 to 20 mg/mL, or 10 to 15 mg/mL, based on the weight of the free base. In a particularly preferred embodiment, when 20 ml of formulation is contained in a single use vial, the formulation comprises approximately 11.76 mg/mL fosnetupitant (based on the weight of the free base) or 13 mg/mL fosnetupitant (based on the weight of the chloride hydrochloride salt). When the formulation is a lyophilized powder the foregoing concentrations are preferably based on a 20 mL reconstitution volume in water.

Various subembodiments can also be defined based on the ratio of netupitant to fosnetupitant in the formulation. The netupitant and fosnetupitant are preferably present in a weight ratio greater than 0.01:99.99 (0.01 weight parts netupitant and 99.99 weight parts fosnetupitant). The weight ratio of netupitant to fosnetupitant is preferably less than 5:95, 4:96, 3:97, 2:98, 1:99, or 0.5:99.5.

Other subembodiments can be defined based on the pH of the formulation. All the present formulations typically have a pH ranging from 7 to 10. In a detailed embodiment, the pH interval ranges from >7.0 up to 10.0. One preferred pH interval is from 8.5 to 9.5. Further sub-ranges are also contemplated, i.e. from >7.0 to 7.5 or from 7.5 to 8.0, or from 8.0 to 8.5, or from 8.5 to 9.0, or from 9.0 to 9.5, or from 9.5 to 10, and combinations of these end-points.

Other subembodiments can be defined based on combinations of acidifying and alkalizing agents used as the "pH adjusting means." At least one alkalizing agent should be present among the pH adjusting means to assure a high enough pH to dissolve the fosnetupitant, but not so high that the fosnetupitant is hydrolyzed to netupitant outside the weight ratios described herein, or other unwanted degradation occurs.

A particularly preferred pH adjusting means is sodium hydroxide, although other alkalizing agents could be used including ammonia, calcium hydroxide, diethanolamine, monoethanolamine, potassium bicarbonate, potassium citrate, potassium hydroxide, sodium bicarbonate, sodium borate, sodium carbonate, sodium citrate dihydrate, dimeglumine, tris(hydroxymethyl)aminomethane, and triethanolamine. Any of these alkalizing agents should be used in a concentration adequate to impart a pH of approximately 11 to 14 (preferably 12) after the addition of fosnetupitant to its target concentration. In a 11.76 mg/mL fosnetupitant formulation (based on the weight of the free base), the sodium hydroxide concentration used for its dissolution will typically range from 1.5 to 3.0 mg/mL, from 2.0 to 2.5 mg/mL, or about 2.18 mg/mL.

The pH adjusting means may also comprise one or more acidifying agents to reduce the pH of the solution after the fosnetupitant is completely solubilized during the manufacturing process, and stabilize the formulation during storage. Exemplary acidifying agents include adipic acid, ammonium chloride, citric acid monohydrate, glacial acetic acid, hydrochloric acid, lactic acid, phosphoric acid, propionic acid, sulfuric acid, tartaric acid, as well as edetic acid and its various salts.

In one embodiment the pH adjusting means includes hydrochloric acid, and it is present if necessary in an amount sufficient to adjust the pH within the range 7 to 10 after the fosnetupitant and sodium hydroxide are combined. Thus, the final amount of added hydrochloric acid will typically equal from 0.5 to 3.0 liters or from 1.0 to 2.0 liters or about 1.5 liters (on a 1.0 M basis) per 300 liters of solution.

In one embodiment the pH adjusting means includes only an alkalizing agent. In another embodiment the pH adjusting means includes an alkalizing agent and an acidifying agent.

In another embodiment, the pH adjusting means includes an alkalizing agent and two acidifying agents.

The above referred amounts of pH adjusting means are herein intended as the amounts used during the manufacturing of the formulation to adjust the pH to the requested pH values; these amounts do not necessarily correspond to those present in the final composition because the pH adjustment involves a consumption of the acidic/basic reagents used for this purpose.

Other subembodiments can be based on the concentration of disodium edetate in the formulation. This component was found surprisingly effective in preventing the hydrolytic conversion of p-Netu to netupitant, as well as unwanted formation of opalescence in the solution after its manufacturing and/or during storage; this advantageously allowed to formulate fosnentupitant at final pH values relatively close to neutrality (a feature particularly appreciated for formulations administrable to patients) without risk of precipitation of fosnentupitant and/or related by-products.

When present in a liquid formulation, the concentration of disodium edetate preferably ranges from 0.05 to 0.9 mg/mL, from 0.1 to 0.25 mg/mL, or from 0.125 to 0.2 mg/mL, based on the anhydrous form. Alternatively, the concentration of disodium edetate preferably ranges from 0.1 to 2.0 mg/mL, from 0.2 to 0.5 mg/mL, or from 0.25 to 0.4 mg/mL. In a first preferred variant, the concentration of disodium edetate is 0.16 mg/mL based on the anhydrous form (or 0.18 mg/mL based on the dihydrate form); another preferred concentration of disodium edetate is 0.32 mg/mL based on the anhydrous form (or 0.35 mg/mL based on the dihydrate form). In a second preferred variant, the preferred concentration of disodium edetate is 0.14 mg/mL based on the anhydrous form (or 0.16 mg/mL based on the dihydrate form); another preferred concentration of disodium edetate is 0.29 mg/mL based on the anhydrous form (or 0.32 mg/mL based on the dihydrate form).

When present in a lyophilized formulation, the concentration of disodium edetate preferably ranges from 0.05 to 0.9 mg/mL, from 0.1 to 0.25 mg/mL, or from 0.125 to 0.2 mg/mL, based on the anhydrous form. Alternatively, the concentration of disodium edetate preferably ranges from 0.1 to 2.0 mg/mL, from 0.2 to 0.5 mg/mL, or from 0.25 to 0.4 mg/mL. In a first preferred variant, the concentration of disodium edetate is 0.16 mg/mL based on the anhydrous form (or 0.18 mg/mL based on the dihydrate form); another preferred concentration of disodium edetate is 0.32 mg/mL based on the anhydrous form (or 0.35 mg/mL based on the dihydrate form). In a second preferred variant, the preferred concentration of disodium edetate is 0.14 mg/mL based on the anhydrous form (or 0.16 mg/mL based on the dihydrate form); another preferred concentration of disodium edetate is 0.29 mg/mL based on the anhydrous form (or 0.32 mg/mL based on the dihydrate form). The foregoing concentrations are based on a suitable reconstitution volume in water, typically 10-30 mL, or 15-25 ml, and most preferably about 20 mL.

The formulation can also include palonosetron or a pharmaceutically acceptable salt thereof, and in a preferred embodiment includes palonosetron hydrochloride. The concentration of palonosetron preferably ranges from 1 to 100 µg/mL, from 2 to 50 µg/mL, from 5 to 50 µg/mL, from 5 to 30 µg/mL, or from 10 to 20 µg/mL, based on the weight of the free base. The palonosetron is most preferably present as palonosetron hydrochloride, and is most preferably present at a concentration of approximately 14.04 µg/mL based on the weight of the hydrochloride salt. When the formulation is a lyophilized powder the foregoing concentrations are based on a suitable reconstitution volume in water, as previously described, typically 10-30 mL, or 15-25 ml, or about 20 mL.

In another embodiment the concentration of palonosetron is proportional to the concentration of netupitant. Thus, in a particularly preferred embodiment the formulation includes 0.28 µg of palonosetron hydrochloride for every 260 mg of the chloride hydrochloride salt of fosnetupitant. In other embodiments, the formulation includes from 0.10 to 1.0 µg or from 0.25 to 0.75 µg of palonosetron hydrochloride (based on the weight of the free base) for every 200 to 450 mg of the chloride hydrochloride salt of fosnetupitant.

Still further subembodiments can be defined based on the bulking agent that can be present in the formulation, and which is always present when the formulation is lyophilized. In various embodiments, the bulking agent comprises mannitol, polyvinylpyrrolidone (PVP), lactose, cellulose, or glycine. A preferred bulking agent is mannitol, and it is preferably present in a concentration of from 10 to 100 mg/mL, from 20 to 70 mg/mL, or from 30 to 50 mg/mL, most preferably 38 mg/mL. When the formulation is a lyophilized powder, this concentration is based on a suitable volume of reconstitution in water, as previously described, typically 10-30 mL, or 15-25 ml, or about 20 mL. The bulking agent also preferably functions as a tonicity agent, and is preferably present in an amount sufficient to render the formulation isotonic.

The formulation is preferably an aqueous-based formulation, with the ingredients combined and dissolved in water for injection. The formulation can also be present as a lyophilized powder. Either formulation is preferably isotonic. The lyophilized formulation preferably has the same active and inactive excipients as the aqueous formulation, in the same relative concentrations, except that the water has been freeze-dried from the formulation; in a variant, the amount of disodium edetate present in lyophilized formulations is higher (typically double) than the amount used in the aqueous formulations.

The formulation is preferably present in a single use container such as a vial, particularly a preservative-free vial, although preservatives could be present, particularly when packaged in a multi-use vial. The formulation and its container are also preferably sterile, during and after packaging. The formulation and container can be aseptically sterilized or terminally sterilized.

When present in a fixed dose container, the formulation can also be characterized by the quantity of fosnetupitant present. Thus, in various subembodiments a single use fixed dose container will contain from about 100 to about 500 mg of fosnetupitant or a pharmaceutically acceptable salt thereof, from about 150 to about 350 mg, or from about 200 to about 300 mg. Most preferably the single use container will contain approximately 235 mg of fosnetupitant or a pharmaceutically acceptable salt thereof, based on the weight of the free base, or approximately 260 mg of the chloride hydrochloride salt of fosnetupitant.

Methods of Treatment

Other subembodiments relate to the use of any of the foregoing formulations for the treatment of diseases modulated by the NK-1 receptor. A particularly preferred use is to treat nausea or emesis, particularly associated with chemotherapy (i.e. chemotherapy induced nausea and vomiting). The New England Journal of Medicine, Vol. 340, No. 3 190-195 (1999) has described the reduction of cisplatin-induced emesis by a selective NK-1 receptor antagonist.

Other uses also are possible. For example, the central and peripheral actions of the mammalian tachykinin substance P, the naturally occurring ligand for the NK-1 receptor, have been associated with numerous inflammatory conditions including migraine, rheumatoid arthritis, asthma, and inflammatory bowel disease as well as the modulation of central nervous system (CNS) disorders such as Parkinson's disease (Neurosci. Res., 1996, 7, 187-214), anxiety (Can. J. Phys., 1997, 75, 612-621) and depression (Science, 1998, 281, 1640-1645). Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases has also emerged ("Tachykinin Receptor and Tachykinin Receptor Antagonists", J. Auton. Pharmacol., 13,23-93, 1993). Other examples of conditions in which substance P has been implicated include disorders of the central nervous system such as anxiety, depression and psychosis. See WO 95/16679, WO 95/18124 and WO 95/23798.

Therefore, in various subembodiments, the invention provides a method of modulating substance-P activity, or treating a disease mediated by substance-P activity, by administering a therapeutically effective dose of any of the foregoing formulations or dosing units. A therapeutically effective dose preferably comprises from 100 to 500 mg of fosnetupitant or a pharmaceutically acceptable salt thereof, and preferably comprises from 200 to 300 mg of fosnetupitant or pharmaceutically acceptable salt thereof. In a particularly preferred embodiment, the therapeutically effective dose comprises 260 mg of the chloride hydrochloride salt of fosnetupitant, administered intravenously, based on the weight of the salt. Preferred diseases treatable by these methods include nausea, emesis and chemotherapy induced nausea and vomiting.

Prior to administration, the formulation is preferably reconstituted with an infusion solution to provide a 30 minute infusion. Suitable infusion solutions include, for example, 5% glucose and 0.9% NaCl. When reconstituted in either of the infusions, the final concentration of fosnetupitant or pharmaceutically acceptable salt thereof will preferably range from 0.5 to 13.0 mg/mL, or from 2.0 to 8.0 mg/mL. In a particular preferred embodiment the concentration in the infusion solution will preferably be approximately 5.2 mg/mL, based on the weight of the chloride hydrochloride salt of fosnetupitant.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention. P-Netu (or API or 08-PNET) refer to the chloride hydrochloride salt of fosnetupitant. Disodium edetate ("EDTA") quantities are reported based on the weight of the dihydrate. 14-netu refers to netupitant. Palo refers to palonosetron HCl with concentrations reported based on the free base Example 1. Effect of Netupitant Concentrations A study was undertaken to determine the maximum allowable concentration of netupitant in aqueous solutions of p-Netu, above which unacceptable precipitation is observed. Based on p-Netu solubility studies indicating that p-Netu solubility drops significantly in water at acidic pH values less than 7.0, and chemical teachings that high pH values will contribute to the hydrolysis of p-Netu to its parent molecule, a solution pH of 7.8 was selected for this example. p-Netu was formulated at a concentration of 13 mg/mL and a pH of 7.8 The results are reported in Table 1.

TABLE 1

| Spiking of Netupitant into p-Netu Solution | Appearance |
| --- | --- |
| 0% | Clear solution |
| 0.5% (0.065 mg/mL) | Clear solution |
| 1% (0.13 mg/mL) | Clear solution |
| 1.5% (0.195 mg/mL) | Slightly opalescent solution |
| 2% (0.26 mg/mL) | Slightly opalescent solution |
| 3% (0.39 mg/mL) | Suspension |
| 4% (0.52 mg/mL) | Suspension |
| 5% (0.65 mg/mL) | Suspension |

Based on these studies, a netupitant concentration of 2.5-3% was determined as the limit for appreciable precipitation in a 13 mg/mL p-Netu solution (maximum ratio ca. 1:50 netu:p-Netu).

Example 2. Formulation Development Studies

Numerous development formulations were prepared and tested, both as liquid solutions and after lyophilization. These studies established the following preliminary trends:

Increasing the API concentration leads to a more degraded lyophilised product.

The mother solutions are more stable than the corresponding freeze dried product; this is surprising for a product susceptible to hydrolytic degradation.

The presence of buffers, especially phosphates, causes greater hydrolysis.

An initial lower concentration of netupitant does not prevent degradation.

Example 3. Factoral Formulation Study

Based on the preliminary results of Example 2, a factorial formulation study was undertaken to investigate the impact of API concentration, disodium edetate and PVP and Tween 80 as surfactants, at pH 8.5-9.5. The formulations are described in Tables 2a and 2b.

TABLE 2a

| Ingredients | F1* Amount | F2 Amount | F3 Amount | F4 Amount | F5 Amount | F6 Amount | F7 Amount | F8 Amount | F9 Amount |
|---|---|---|---|---|---|---|---|---|---|
| API | | | | | | | | | |
| 08-PNET (mg/mL) | 5 | 26 | 15.5 | 5 | 26 | 26 | 26 | 5 | 5 |
| Excipients | | | | | | | | | |
| PVP K12 (% v/v) | 0 | 0 | 1 | 0 | 2 | 2 | 0 | 2 | 2 |
| EDTA disodium salt (% w/v) | 0.127 | 0.127 | 0.064 | 0 | 0 | 0.127 | 0 | 0 | 0.127 |
| Tween 80 (% w/v) | 0 | 0.5 | 0.25 | 0.5 | 0.5 | 0 | 0 | 0 | 0.5 |

TABLE 2b

| Ingredients | F10 Amount | F11 Amount | F12 Amount | F13 Amount | F14 Amount | F15 Amount | F16 Amount | F17 Amount | F18 Amount | F19 Amount |
|---|---|---|---|---|---|---|---|---|---|---|
| API | | | | | | | | | | |
| 08-PNET (mg/mL) | 5 | 26 | 26 | 26 | 5 | 15.5 | 5 | 5 | 26 | 15.5 |
| Excipients | | | | | | | | | | |
| PVP K12 (% v/v) | 0 | 2 | 2 | NA | 2 | 1 | 0 | 2 | 0 | 0 |
| EDTA disodium salt (% w/v) | 0 | 0 | 0.127 | 0.127 | 0.127 | 0.064 | 0.127 | 0 | 0 | 0 |
| Tween 80 (% w/v) | 0 | 0 | 0.50 | 0 | 0 | 0.25 | 0.50 | 0.50 | 0.50 | 0 |

The solutions were evaluated for a month at 40° C. and 75% RH and at 25° C. and 60% relative humidity. After 30 days all the solutions at 40° C. were clear and about half of those at room temperature were limpid. The results are presented in Table 2c.

TABLE 2c

| | Storage Conditions (30 days) | %14-Netu amount |
|---|---|---|
| F1 | 40° C./75% RH | 1.2 |
| | 25° C./60% RH | 1.2 |
| F1b | 40° C./75% RH | 1.5 |
| | 25° C./60% RH | 1.3 |
| F2 | 40° C./75% RH | 1.3 |
| | 25° C./60% RH | opalescent |
| F3 | 40° C./75% RH | 1.4 |
| | 25° C./60% RH | 1.2 |
| F4 | 40° C./75% RH | 1.2 |
| | 25° C./60% RH | 0.9 |
| F5 | 40° C./75% RH | 1.5 |
| | 25° C./60% RH | opalescent |
| F6 | 40° C./75% RH | 1.4 |
| | 25° C./60% RH | opalescent |
| F7 | 40° C./75% RH | 1.5 |
| | 25° C./60% RH | opalescent |
| F8 | 40° C./75% RH | 1.8 |
| | 25° C./60% RH | opalescent |
| F9 | 40° C./75% RH | 1.0 |
| | 25° C./60% RH | 0.9 |
| F10 | 40° C./75% RH | 1.7 |
| | 25° C./60% RH | 1.8 |
| F11 | 40° C./75% RH | 1.5 |
| | 25° C./60% RH | opalescent |
| F12 | 40° C./75% RH | 1.4 |
| | 25° C./60% RH | opalescent |
| F13 | 40° C./75% RH | 1.5 |
| | 25° C./60% RH | opalescent |
| F14 | 40° C./75% RH | 1.4 |
| | 25° C./60% RH | opalescent |
| F15 | 40° C./75% RH | 1.4 |
| | 25° C./60% RH | 1.2 |

TABLE 2c-continued

| | Storage Conditions (30 days) | %14-Netu amount |
|---|---|---|
| F16 | 40° C./75% RH | 1.2 |
| | 25° C./60% RH | 0.9 |
| F17 | 40° C./75% RH | 2.9 |
| | 25° C./60% RH | 1.0 |
| F18 | 40° C./75% RH | 1.6 |
| | 25° C./60% RH | opalescent |
| F19 | 40° C./75% RH | 1.5 |
| | 25° C./60% RH | 1.3 |

Further experiments have shown that the presence of EDTA reduced, in proportion to its concentration in solution, the conversion of p-Netu to 14-Netu, with a corresponding stabilization of the solution which remained clear throughout the whole testing period.

Example 4. Exemplary Formulations

Exemplary lyophilized and liquid formulations based on the studies described in the previous examples are presented below in Tables 3a to 3c; in these tables the quantities of EDTA are based on its dihydrated disodium salt.

TABLE 3a (lyophilized formulation)

| Ingredient | Concentration | Purpose |
|---|---|---|
| p-Netu | 13 mg/mL | Active |
| Palo HCl (optional) | 14.04 µg/mL | Active |
| EDTA | 0.32 mg/mL | Chelating agent |
| Mannitol | 38 mg/mL | Bulking agent |

TABLE 3a-continued (lyophilized formulation)

| Ingredient | Concentration | Purpose |
|---|---|---|
| NaOH (0.5M) | q.s. for p-Netu dissolution and pH adjustment | p-Netu dissolution and pH adjustment |
| HCl (0.1M and 1.0M) | q.s. for pH adjustment | pH adjustment |
| WFI | q.s. to 1 mL | Solvent (removed during lyophilization) |

The lyophilized product unit contains 20 times the above amounts, to be reconstituted with 20 mL of water
\* 13 mg of p-Netu corresponding to 11.8 mg fosnetupitant free base (Ratio 1.106:1)
\*\* 14.04 µg of palonosetron HCl corresponding to 12.5 µg of palonosetron free base (Ratio 1.123:1)

TABLE 3b (liquid injectable formulation)

| Ingredient | Concentration | Amount per vial \*\*\* |
|---|---|---|
| p-Netu | 26 mg/mL | 273 mg \* |
| Palo HCl (optional) | 28.08 µg/mL | 294.84 µg \*\* |
| EDTA | 0.32 mg/mL | 3.36 mg |
| Mannitol | 25 mg/mL | 262.5 mg |
| NaOH (0.5M) | q.s. for p-Netu dissolution | |
| HCl (0.1M and 1.0M) | q.s. for pH adjustment | |
| WFI | q.s. to 1 mL | 10.5 mL |

10.5 mL of the solution are used for filling the Vial
\* 273 mg of p-Netu corresponding to 246.8 mg fosnetupitant free base (Ratio 1.106:1)
\*\* 294.84 µg of palonosetron HCl corresponding to 262.5 µg of palonosetron free base (Ratio 1.123:1)
\*\*\* Labeled amounts: 260.0 mg of fosnetupitant and 0.250 mg of palonosetron free base

TABLE 3c (liquid injectable formulation)

| Ingredient | Concentration | Amount per vial \*\*\* |
|---|---|---|
| p-Netu | 13 mg/mL | 267.8 mg \* |
| Palo HCl (optional) | 14.04 µg/mL | 289.22 µg \*\* |
| EDTA | 0.16 mg/mL | 3.30 mg |
| Mannitol | 38 mg/mL | 782.8 mg |
| NaOH (0.5M) | q.s. for p-Netu dissolution | |
| HCl (0.1M and 1.0M) | q.s. for pH adjustment | |
| WFI | q.s. to 1 mL | 20.6 mL |

20.6 mL of the solution are used for filling the Vial
\* 267.8 mg of p-Netu corresponding to 242.1 mg fosnetupitant free base (Ratio 1.106:1)
\*\* 289.22 µg of palonosetron HCl corresponding to 257.5 µg of palonosetron free base (Ratio 1.123:1)
\*\*\* Labeled amounts: 260.0 mg of fosnetupitant and 0.250 mg of palonosetron free base Three further formulations were prepared (the first being a lyophilized formulation while the second and third being liquid injectable formulations) whose compositions were identical to those respectively reported in Tables 3a, 3b and 3c, with the sole difference that the weight of EDTA disodium salt (i.e. 0.32, 0.32 and 0.16 mg/mL respectively) was that of the anhydrous product (i.e. the EDTA disodium salt in its non-hydrated form): each of these formulations represents a further embodiment of the present invention.

Example 5. Manufacturing Protocol

Figure 2:
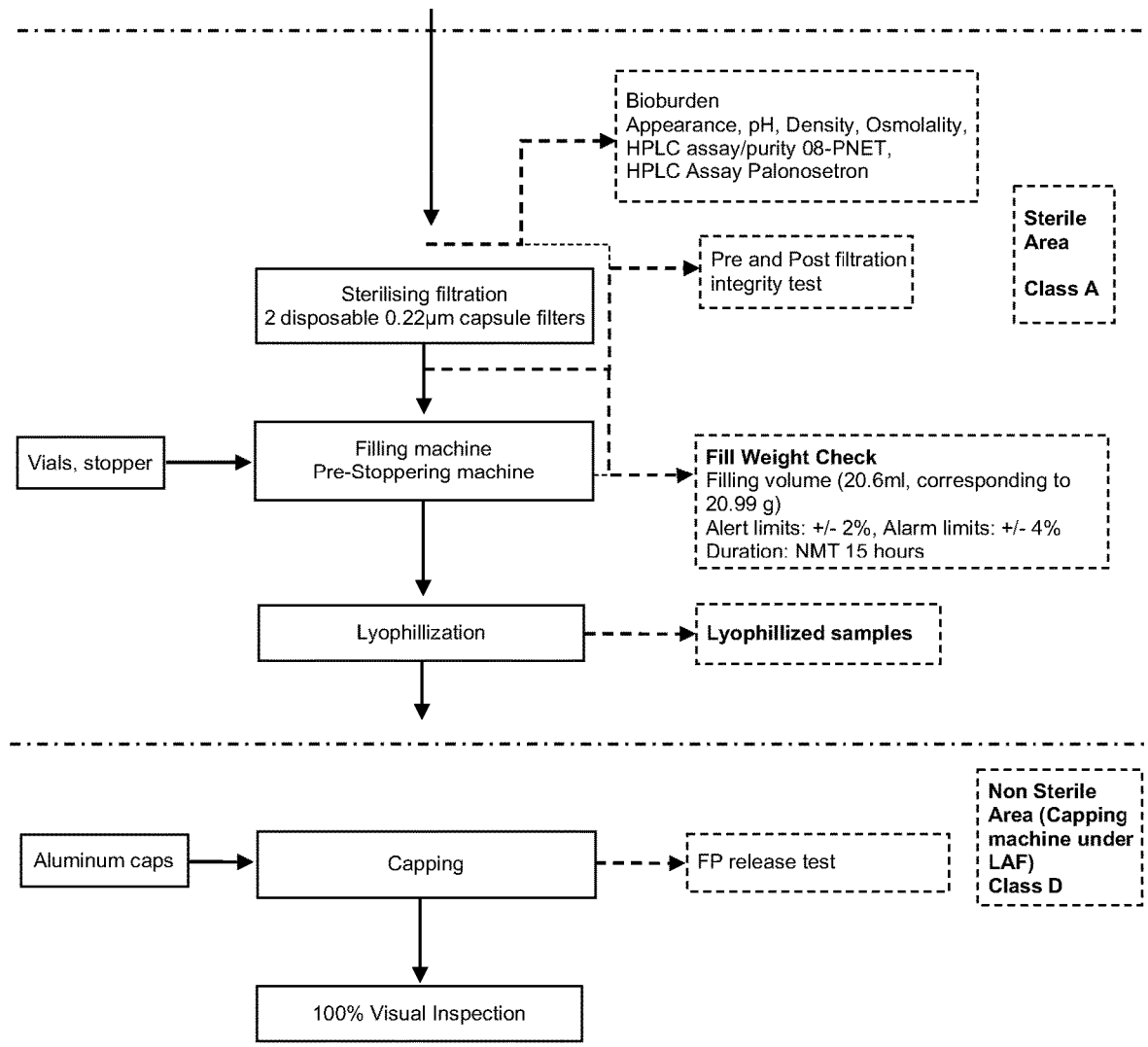

The protocol for manufacturing the formulation described in Example 4 is described below and depicted in FIGS. 1 and 2. Two 325 liter tanks are used to carry out solution preparation. The mixing system of the compounding vessel consists of a magnetic stirring system. This system is equipped with a propeller-shaped mixing head placed at the bottom of the tank and moved by a magnetic rotating field. The preparation steps are as follows:

1. The compounding vessel is loaded with WFI (at 20±5° C.) up to a mass of 40±1 kg.
2. 654 g of solid NaOH is added to the compounding vessel.
3. After the dissolution of the NaOH, the compounding vessel is loaded with WFI (at 20±5° C.) up to a mass of 183 kg±1 kg (ca. 60% of the final volume).
4. The solution is mixed for 10 minutes. The pH of the solution in the compounding vessel is raised to the target pH of ca.13 (pH range: 11-14).
5. p-Netu is slowly added inside the compounding tank.
6. pH is checked at room temperature (22±5° C.). Because the addition of p-Netu tends to lower the pH, manual titration can be performed using an amount of NaOH 0.5M to reach a pH value within the range 9-13, with 12 as the target pH.
7. After the dissolution of the p-Netu, pH is checked at room temperature (22±1° C.) and adjusted if necessary to the range 9-13, with 12 as target point.
8. 96 g of EDTA disodium salt dihydrate is added to the compounding tank and the solution stirred until complete dissolution.
9. After EDTA addition, pH is checked at room temperature (24±1° C.) and adjusted if necessary to 9.00±0.50 with HCl (0.1 and 1.0M) or NaOH 0.5M.
10. 11.4 kg of mannitol is added to the compounding tank.
11. The palonosetron HCl weighed in the dispensing area is solubilized in a glass beaker using 490 g of WFI, in p-Netu-Palo Combo solution preparation room.
12. Palonosetron HCl solution is added inside the compounding tank.
13. After palonosetron HCl addition, pH is checked again at room temperature (24° C.±1) and adjusted if necessary to 9.00±0.50 with HCl (0.1 and 1.0M) or NaOH 0.5M.
14. Eventually, the final QS weight is achieved by loading WFI into the tank at RT.
15. The p-Netu-Palo combination solution is brought to the final volume (300 L→305.7 kg) by means of WFI.

Lyophilization is undertaken using a standard lyophilization cycle. Briefly, the lyophilization cycle takes place in a 33 m² BOC Edwards freeze-dryer using bottomless trays. The partially stoppered vials are loaded into the BOC Edwards 33" freeze dryer at 5±3° C. Each tray is loaded with 47 vials and each shelf with 30 bottomless trays. When drying is completed, sterile filtered nitrogen is injected into the chamber through a sterile 0.22 micron filter. The vials are automatically stoppered in the chamber, unloaded, and then transported by means of a laminar flow trolley to the capping machine where the vials are loaded on a turntable (which feed the capping machine).

Example 6. Stability Testing

The lyophilized and liquid formulations as described in Example 4 were tested for stability and the results reported below in Tables 4a, 4b and 4c.

TABLE 4a (lyophilized formulation of Example 4, table 3a)

| Test | T = 0 | 1M-<br>25° C./60% RH;<br>30° C./65% RH;<br>40° C./75% RH | 3M 5° C.;<br>25° C./60% RH;<br>30° C./65% RH | 6M 5° C.;<br>25° C./60% RH;<br>30° C./65% RH | 12M 5° C.;<br>25° C./60% RH | 18M 5° C. | 24M 5° C. |
|---|---|---|---|---|---|---|---|
| pH | 9.6 | —<br>9.8<br>9.8<br>9.6 | 9.7<br>9.6<br>9.6<br>— | 9.6<br>9.7<br>9.5<br>— | 9.7<br>9.5<br>—<br>— | 9.7<br>—<br>—<br>— | 9.7<br>—<br>—<br>— |
| Appearance reconstituted solution | Clear | —<br>clear<br>clear<br>clear | —<br>clear<br>clear<br>— | clear<br>clear<br>clear<br>— | clear<br>clear<br>—<br>— | clear<br>—<br>—<br>— | clear<br>—<br>—<br>— |
| Osmolarity | 336 | —<br>302<br>302<br>296 | 317<br>312<br>309<br>— | 308<br>330<br>312<br>— | 308<br>320<br>—<br>— | 316<br>—<br>—<br>— | 303<br>—<br>—<br>— |
| KF (%) | 0.29 | —<br>0.48<br>0.44<br>0.40 | 0.36<br>0.40<br>0.46<br>— | 0.34<br>0.44<br>0.52<br>— | 0.31<br>0.65<br>—<br>— | 0.29<br>—<br>—<br>— | 0.35<br>—<br>—<br>— |
| %14-Netu | 0.82 | —<br>1.07<br>1.30<br>2.50 | 0.76<br>1.33<br>1.97<br>— | 0.87<br>1.76<br>2.81<br>— | 0.85<br>2.59<br>—<br>— | 0.87<br>—<br>—<br>— | 0.97<br>—<br>—<br>— |
| Assay 08-PNET (mg/vial) | 270.4 | —<br>262.6<br>259.4<br>257.3 | 259.9<br>258.3<br>260.8<br>— | 262.7<br>260.8<br>253.6<br>— | 270.0<br>269.5<br>—<br>— | 261.2<br>—<br>—<br>— | 255.6<br>—<br>—<br>— |
| Assay Palo (mg/vial) | 0.245 | —<br>0.247<br>0.245<br>0.237 | 0.255<br>0.250<br>0.249<br>— | 0.254<br>0.252<br>0.250<br>— | 0.271<br>0.248<br>—<br>— | 0.252<br>—<br>—<br>— | 0.239<br>—<br>—<br>— |
| Related Substances % (Palo) | — | —<br>—<br>—<br>— | —<br>—<br>—<br>— | <LOQ<br><LOQ<br><LOQ<br>— | <LOQ<br><LOQ<br>—<br>— | <LOQ<br>—<br>—<br>— | <LOQ<br>—<br>—<br>— |

TABLE 4b (lyophilized formulation of Example 4, table 3b)

| Test | T = 0 | 1M-<br>25° C./60% RH;<br>30° C./65% RH;<br>40° C./75% RH | 3M 5° C.;<br>25° C./60% RH;<br>30° C./65% RH | 6M 5° C.;<br>25° C./60% RH;<br>30° C./65% RH | 9M 5° C.;<br>25° C./60% RH | 12M 5° C. |
|---|---|---|---|---|---|---|
| pH | 9.4 | 9.2<br>9.2<br>9.2 | 9.3<br>9.3<br>9.2 | 9.3<br>9.2<br>9.0 | 9.2<br>—<br>— | 9.3<br>—<br>— |
| Appearance reconstituted | clear | clear<br>clear<br>clear | clear<br>clear<br>clear | clear<br>clear<br>clear | clear<br>—<br>— | clear<br>—<br>— |
| Osmolarity (mOsm/kg) | 303 | 309<br>313<br>308 | 313<br>310<br>313 | 312<br>312<br>313 | 313<br>—<br>— | 312<br>—<br>— |
| %14-Netu | 0.46 | 0.57<br>0.58<br>0.73 | 0.58<br>0.61<br>0.93 | 0.60<br>0.66<br>1.21 | 0.54<br>—<br>— | 0.63<br>—<br>— |
| Assay 08-PNET (mg/ml) | 26.3 | 25.6<br>26.1<br>28.3 | 26.6<br>26.7<br>26.6 | 26.1<br>26.1<br>25.8 | 26.4<br>—<br>— | 25.2<br>—<br>— |
| Assay Palo (mg/ml) | 0.025 | 0.024<br>0.024<br>0.024 | 0.025<br>0.025<br>0.024 | 0.025<br>0.025<br>0.024 | 0.024<br>—<br>— | 0.024<br>—<br>— |
| Related Substances % (Palo) | Not detectable | <LOQ<br><LOQ<br><LOQ | <LOQ<br>RRT 0.32:0.61<br>08-PALOd1:0.40<br>RRT 0.32:0.44 | <LOQ<br><LOQ<br>08-PALOd1:0.62 | RRT 0.28:0.42<br>—<br>— | RRT 0.28:0.47<br>RRT 0.32:0.42<br>— |

TABLE 4c (lyophilized formulation of Example 4, table 3c)

| Test | T = 0 | 1M 25° C./60% RH; 1M 30° C./65% RH; 1M 40° C./75% RH | 3M 25° C./60% RH; 3M 30° C./65% RH 3M 40° C./75% RH | 6M 25° C./60% RH; 6M 30° C./65% RH; 6M 40° C./75% RH | 9M 25° C./60% RH | 12M 25° C./60% RH | 18M 25° C./60% RH |
|---|---|---|---|---|---|---|---|
| pH | 9.4 | 9.1<br>9.1<br>9.0 | 9.1<br>9.1<br>8.9 | 9.1<br>9.1<br>8.8 | 9.0 | 9.1 | — |
| Appearance of solution (5° C. clear without visible particles) | clear | clear<br>clear<br>clear | clear<br>clear<br>clear | clear<br>clear<br>clear | clear | clear | — |
| Osmolarity (mOsm/kg) | 296 | 320<br>302<br>304 | 306<br>306<br>307 | 307<br>307<br>307 | 317 | 308 | — |
| %14-Netu | 0.46 | 0.55<br>0.56<br>0.67 | 0.59<br>0.62<br>0.96 | 0.59<br>0.66<br>1.32 | 0.65 | 0.65 | — |
| Assay 08-PNET (mg/ml) | 13.0 | 13.1<br>13.2<br>13.2 | 13.3<br>13.3<br>13.2 | 13.1<br>13.0<br>13.2 | 13.2 | 12.7 | — |
| Assay Palo (mg/ml) | | 0.0127<br>0.0125<br>0.0124 | 0.0128<br>0.0127<br>0.0126 | 0.0125<br>0.0125<br>0.0123 | 0.0123 | 0.0124 | — |
| Related Substances % (Palo) | <LOQ | <LOQ<br><LOQ<br><LOQ | <LOQ<br><LOQ<br><LOQ | <LOQ<br><LOQ<br><LOQ | <LOQ | 0.40 | — |

OTHER EMBODIMENTS

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A pharmaceutically stable injectable liquid formulation of fosnetupitant comprising:
    a) from 2.3 to 30 mg/mL of the chloride hydrochloride salt of fosnetupitant;
    b) from 5 to 50 µg/mL palonosetron hydrochloride based on the weight of the free base;
    c) sodium hydroxide;
    d) disodium edetate;
    e) optionally hydrochloric acid; and
    f) mannitol.

2. A pharmaceutically stable injectable lyophilized formulation of fosnetupitant comprising:
    a) from 2.3 to 30 mg/mL of the chloride hydrochloride salt of fosnetupitant;
    b) from 5 to 50 µg/mL palonosetron hydrochloride based on the weight of the free base;
    c) sodium hydroxide;
    d) disodium edetate;
    e) optionally hydrochloric acid; and
    f) mannitol.

3. A pharmaceutically stable liquid injectable solution formulation of fosnetupitant at a pH of 7.0-10.0 comprising:
    a) from 2.3 to 30 mg/mL of the chloride hydrochloride salt of fosnetupitant;
    b) from 5 to 50 µg/mL palonosetron hydrochloride based on the weight of the free base;
    c) from 0.05 to 0.9 mg/mL disodium edetate;
    d) from 10 to 100 mg/mL mannitol;
    e) NaOH;
    optionally HCl; and
    g) water q.s.

4. A pharmaceutically stable lyophilized powder injectable formulation of fosnetupitant at a pH of 7.0-10.0 comprising:
    a) from 2.3 to 30 mg/mL of the chloride hydrochloride salt of fosnetupitant;
    b) from 5 to 50 µg/mL palonosetron hydrochloride based on the weight of the free base;
    c) from 0.1 to 2.0 mg/mL disodium edetate;
    d) from 10 to 100 mg/mL mannitol; and
    e) NaOH and optionally HCl;
    based on a reconstitution in a suitable water volume.

5. The lyophilized powder formulation of claim 4 at a pH of 7.0-10.0, comprising:
    a) from 2.3 to 30 mg/mL of the chloride hydrochloride salt of fosnetupitant;
    b) from 5 to 50 µg/mL palonosetron hydrochloride based on the weight of the free base;
    c) from 0.1 to 2.0 mg/mL disodium edetate;
    d) from 10 to 100 mg/mL mannitol; and
    e) NaOH and HCl;
    based on a reconstitution in a suitable water volume.

6. The lyophilized powder formulation of claim 4 at a pH of 8.5-9.5, comprising:
    a) about 13.0 mg/mL of the chloride hydrochloride salt of fosnetupitant;
    b) about 14.04 µg/mL palonosetron hydrochloride based on the weight of the salt;
    c) about 0.32 mg/mL disodium edetate;
    d) about 38 mg/mL mannitol; and
    e) NaOH and optionally HCl;
    based on a reconstitution in water volume of 20 mL.

7. A method of manufacturing a liquid injectable or lyophilized formulation of fosnetupitant comprising:
    a) simultaneously admixing the chloride hydrochloride salt of fosnetupitant with sodium hydroxide in water at a basic pH of from approximately 11 to 14 to form a solution;

b) reducing the pH of the solution to a basic pH of from approximately 7 to 10 by the addition of one or more acidic pH adjusting agents; and c) optionally admixing the solution with one or more pharmaceutically acceptable excipients.

8. An intravenous formulation of fosnetupitant made by a process of mixing the fosnetupitant formulation of claim 2 with 0.9% saline or 5% glucose.

9. The liquid formulation of claim 1 comprising palonosetron hydrochloride and HCl.

10. The liquid formulation of claim 3, comprising:
   a) from 2.3 to 30 mg/mL of the chloride hydrochloride salt of fosnetupitant;
   b) from 5 to 50 μg/mL palonosetron hydrochloride based on the weight of the free base;
   c) from 0.1 to 2.0 mg/mL disodium edetate;
   d) from 10 to 100 mg/mL mannitol; and
   e) NaOH and HCl.

11. The liquid formulation of claim 3 at a pH of 8.5-9.5, comprising:
   a) about 13.0 mg/mL of the chloride hydrochloride salt of fosnetupitant;
   b) about 14.04 μg/mL palonosetron hydrochloride based on the weight of the salt;
   c) about 0.32 mg/mL disodium edetate;
   d) about 38 mg/mL mannitol; and
   e) NaOH and HCl.

12. The lyophilized powder formulation of claim 2 comprising:
   a) from 2.3 to 30 mg/mL of the chloride hydrochloride salt of fosnetupitant;
   b) from 5 to 50 μg/mL palonosetron hydrochloride based on the weight of the free base;
   c) from 0.1 to 2.0 mg/mL disodium edetate;
   d) from 10 to 100 mg/mL mannitol; and
   e) NaOH and optionally HCl;
   based on a reconstitution in a suitable water volume.

13. The lyophilized powder formulation of claim 2 comprising:
   a) about 13.0 mg/mL of the chloride hydrochloride salt of fosnetupitant;
   b) about 14.04 μg/mL palonosetron hydrochloride based on the weight of the salt;
   c) about 0.32 mg/mL disodium edetate;
   d) about 38 mg/mL mannitol; and
   e) NaOH and HCl;
   based on a reconstitution in a suitable volume of water.

14. The liquid formulation of claim 1 at a pH of from 7.5 to 10.0.

15. The lyophilized powder formulation of claim 2 having a pH of from 7.5 to 10.0 upon reconstitution in water.

16. The lyophilized powder formulation of claim 12 having a pH of from 7.5 to 10.0 upon reconstitution in water.

17. The lyophilized powder formulation of claim 13 having a pH of from 7.5 to 10.0 upon reconstitution in water.

18. The method of claim 7, wherein the acidic pH adjusting agent comprises hydrochloric acid.

19. A pharmaceutically stable injectable liquid formulation of fosnetupitant comprising:
   a) from 2.3 to 30 mg/mL of the chloride hydrochloride salt of fosnetupitant;
   b) from 5 to 50 μg/mL palonosetron hydrochloride based on the weight of the free base;
   c) an alkalizing agent; and
   d) an alkaline pH.

20. The pharmaceutically stable injectable liquid formulation of claim 19 comprising:
   a) about 13.0 mg/mL of the chloride hydrochloride salt of fosnetupitant;
   b) about 14.04 μg/mL palonosetron hydrochloride based on the weight of the salt;
   c) sodium hydroxide as the alkalizing agent; and
   d) a pH of from 7 to 10.

21. The pharmaceutically stable injectable liquid formulation of claim 19 comprising sodium hydroxide as the alkalizing agent and a pH of from 7 to 10.

\* \* \* \* \*

UNITED STATES PATENT AND TRADEMARK OFFICE
CERTIFICATE OF CORRECTION

PATENT NO. : 10,624,911 B2
APPLICATION NO. : 15/611785
DATED : April 21, 2020
INVENTOR(S) : Alessio Venturini and Roberta Cannella It is certified that error appears in the above-identified patent and that said Letters Patent is hereby corrected as shown below:

In the Specification

In Column 17/18, Table 4b, in the second line of the header, replace "lyophilized" with --liquid injectable--

In Column 19/20, Table 4c, in the second line of the header, replace "lyophilized" with --liquid injectable--

Signed and Sealed this
Twenty-fourth Day of January, 2023

Katherine Kelly Vidal
Director of the United States Patent and Trademark Office